United States Patent [19]

Sommer et al.

[11] 4,150,245
[45] Apr. 17, 1979

[54] HYDRATION OF OLEFINS USING VAPORIZED PHOSPHORIC ACID

[75] Inventors: August Sommer, Herne; Rainer Brücker, Castrop-Rauxel; Wilhelm Heitmann, Herne, all of Fed. Rep. of Germany

[73] Assignee: Veba-Chemie Aktiengesellschaft, Gelsenkirchen-Buer, Fed. Rep. of Germany

[21] Appl. No.: 864,062

[22] Filed: Dec. 23, 1977

[30] Foreign Application Priority Data

Dec. 24, 1976 [DE] Fed. Rep. of Germany ....... 2658946

[51] Int. Cl.$^2$ ............................................. C07C 29/08
[52] U.S. Cl. ................................................... 568/896
[58] Field of Search ................................ 568/896, 898

[56] References Cited

U.S. PATENT DOCUMENTS

| | | | |
|---|---|---|---|
| 2,579,601 | 12/1951 | Nelson et al. | 568/896 |
| 3,784,614 | 1/1974 | Ester et al. | 568/896 |
| 3,898,290 | 8/1975 | Ester | 568/896 |

*Primary Examiner*—Joseph E. Evans
*Attorney, Agent, or Firm*—Sprung, Felfe, Horn, Lynch & Kramer

[57] ABSTRACT

A process for the hydration of olefins to prepare alcohol is disclosed, the hydration being effected in the presence of a phosphorus acid-containing catalyst. There is disclosed a process in which vaporized phosphoric acid is admixed with a gas mixture before the same is added to the reactor, the phosphoric acid being in an amount corresponding to the amount of phosphoric acid discharged during the hydration. In such amount the process can be carried out without further phosphoric acid addition.

3 Claims, 1 Drawing Figure

VIEW A    SECTION B-C

FIG. I.
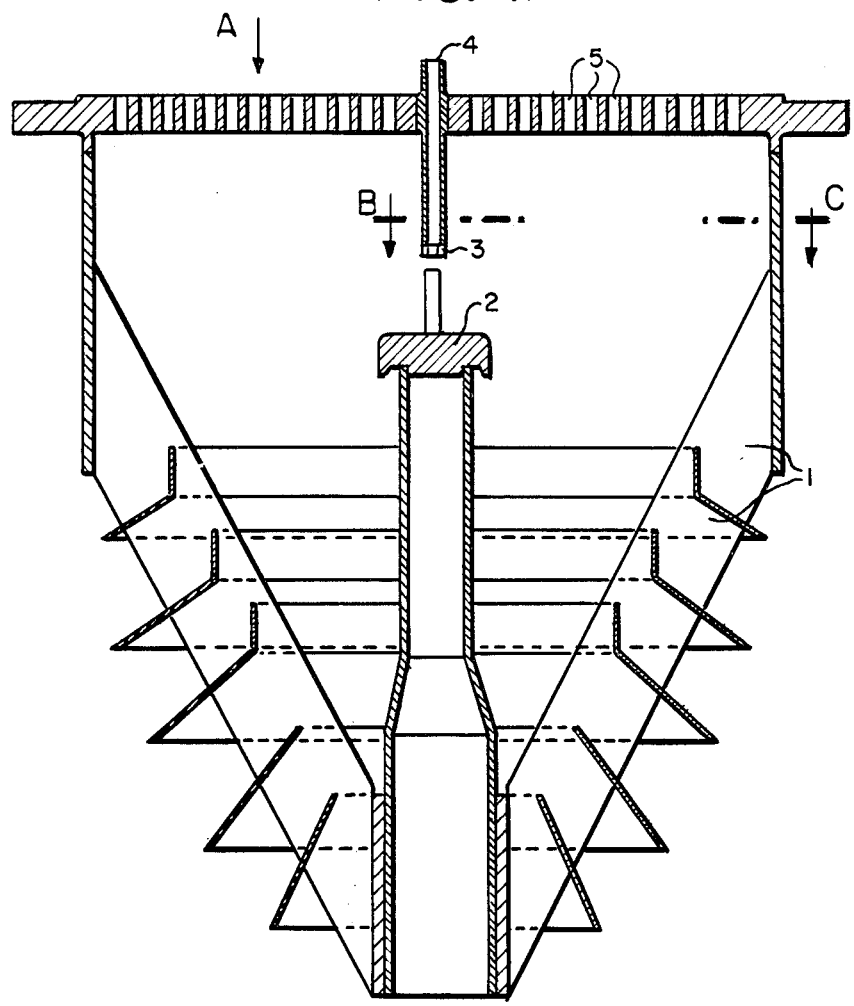
VIEW A
SECTION B-C
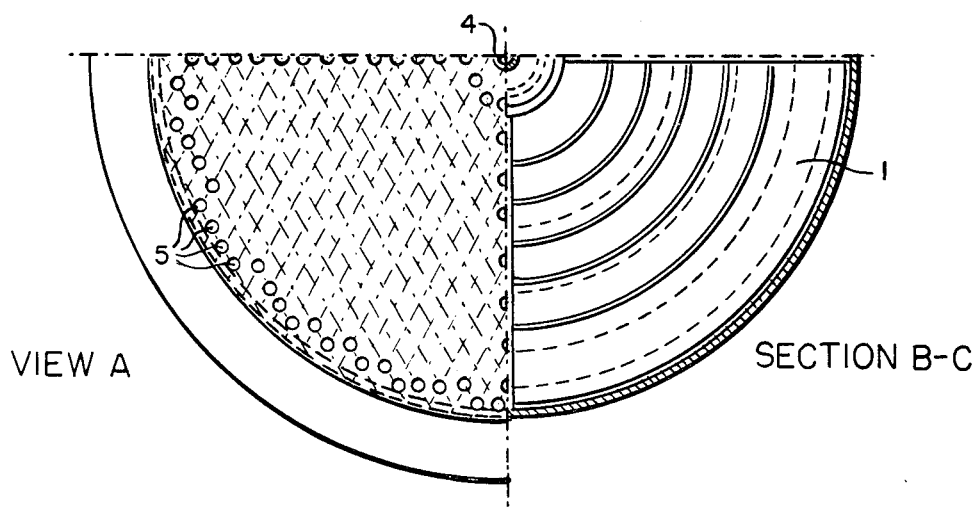

HYDRATION OF OLEFINS USING VAPORIZED PHOSPHORIC ACID

The invention is concerned with the preparation of alcohols by catalytic hydration of olefins whereby there is added to the reactor simultaneously with the starting gas the amount of catalyst which is normally discharged during the passage of the starting gas through the catalyst/support mass, preponderantly by being carried along in the evaporated stage according to the steam pressure.

It is known to prepare aliphatic alcohols synthetically by conducting olefins together with water vapor over catalysts. As such a catalyst there is especially considered phosphoric acid which is attached to porous supports (contact mass). It is also known that the discharge of phosphoric acid during the reaction which takes place at elevated temperature and elevated pressure, the activity of the contact mass will decrease rapidly. This decrease in activity depends on the amount of phosphoric acid discharged with the reaction gas. This discharged amount of phosphoric acid is again dependent on the reaction conditions such as mol ratio of water to olefin in the starting gas, temperature, pressure and the type of porous support. The reaction temperature is reduced due to the fact that the phosphoric acid amount on the support is kept so small that there is free volume in the pores, and the kind of mol ratio of water to olefin is chosen which ensures that all of the water is only present in the vaporous aggregated condition if it enters the reactor together with the olefin, the discharged amount of phosphoric acid can be lowered considerably because especially by reduction of the amount of phosphoric acid on the support and the adjusted mol ratio of water to olefin in the reactor entry gas, it can be avoided that such phosphoric acid is discharged which is dislodged from its place in the pore volume of the support by the adjustment of the concentration of the equilibrium under reaction conditions, which lies below the starting concentration, to some extent by the dilution water entering through the pore volume of the support, and is carried along by the gas stream in liquid form (German Pat. No. 1,249,845).

Despite this measure, the activity loss is so big that during the course of several months the synthesis equipment has to be shut down and made pressureless in order to add, in any manner, newly activated contact in place of that depleted of phosphoric acid. It has also been suggested to maintain the activity of the mass over an extended period of time (U.S. Pat. No. 2,579,601) by continuous or alternating addition of phosphoric acid to the contact mass is an amount corresponding to a part by weight of phosphoric acid calculated at 100% to about 150 to 250 parts by weight of produced alcohol. The above-described, already quite favorable adjustment of the phosphoric acid amount on the support and the smaller phosphoric acid discharge connected therewith cannot be achieved by this measure since, in view of the kind of the addition, the surface of the contact mass will surely be completely sprinkled with acid. According to this known process, a clear decrease in activity of the contact will still take place if amounts of phosphoric acid smaller than 1:250 parts by weight of phosphoric acid are added per weight part of produced alcohol so that a ratio of added phosphoric acid to produced alcohol of below 1:400 did not seem meaningful and was also not used. It is reported that with a phosphoric acid addition at the ratio of 1:150 to 250 to the amount of alcohol produced, one can work with a contact mass for close to five months without having to shut off the equipment, with a satisfactory reaction (3.2–4% of the ethylene inserted). The state of the art of the continuous feeding of larger or smaller amounts of liquid phosphoric acid to the contact mass is expressed, for instance, in U.S. Pat. No. 3,704,329, German Pat. No. 1,293,233. German OS No. 1,643,025 has been subject matter the recycling of the portion liquefied by condensation of the phosphoric acid discharged with the reaction stream in liquid form to the catalyst mass. The second claim of German OS No. 2,065,569 concerns the addition of phosphoric acid lost during the reaction. Since the value is calculated in Example 1 with 713 kilo ethanol per kilo of 100% calculated phosphoric acid, i.e., substantially more phosphoric acid is added than according to this application, one must assume that, because of the addition of liquid phosphoric acid, more acid is continuously removed than corresponds to the steam pressure, and the maximal free surface is thus not available for the activity of the catalyst, which is maintained during the application of the phosphoric acid in vaporized condition.

Another suggestion according to German Pat. No. 967,343 is directed to changing the flow direction of the reaction gas about every two weeks by way of the contact mass since a depletion of the mass of phosphoric acid preferably takes place in the vicinity of the reaction gas entry. The distribution of the unremoved phosphoric acid is to be equalized on the contact mass by the continuous changing of the flow direction. Although it is not exactly stated in the patent for how long a contact mass can be conducted in this manner with satisfactory reaction without the shutting off of the equipment, several months are mentioned. In view of the amount of discharged phosphoric acid mentioned, which is not replaced, it can be assumed, however, that this is also no more than five months. The process thus described has substantial disadvantages on a large commercial scale since unavailable tight shut-off valves are required in the high pressure gas stream for the switching. In addition, the catalyst space for the inert material is increased by this suggestion, and only liquidly discharged phosphoric acid is retained.

Therefore, it was the problem of the invention to develop a process wherein amounts as small as possible of phosphoric acid are discharged.

Surprisingly, it was discovered thereby that one can maintain the contact activity for a substantially longer period of time, 1 to 2 years in case of ethanol, over four years with isopropyl alcohol, for an olefin reaction of over 4%, if one adds a small amount of phosphoric acid to the contact mass not liquidly but admixes it to the reaction gas mixture entering the reactor prior to the entry into the reactor before the gas comes in contact with the contact mass. In this manner, already discharged phosphoric acid in not replaced on the support or newly distributed, as in the case of the hitherto known processes, but, as must be assumed from the observations, the evaporation of phosphoric acid otherwise occurring on the support is avoided by the $H_3PO_4$ partial pressure in the gas flowing in, which corresponds to the equilibrium steam pressure at the prevailing temperature. In this manner, the activity of the contact is maintained longer than when the places from which phosphoric acid was removed are to be resaturated by spraying on liquid acid.

The subject matter in the invention is therefore a process for the production of alcohols having 2-3 carbon atoms by way of catalytic hydration of olefins by reaction on phosphorus-containing catalysts, characterized in that phosphoric acid is added to the gas mixture before entry into the reactor in an amount corresponding to the ascertained amount of removed phosphoric acid without further addition of acid during the reaction.

In the case of ethanol, the preferred amount of phosphoric acid to be added is 1 weight part (100% $H_3PO_4$) to 800 to 1,500 weight parts of produced alcohol, in the case of isopropyl alcohol 1 weight part to 8,000 to 15,000 weight parts.

In attempts to solve the problem it was first established that with constant working conditions of longer duration, after implementation of the improvements mentioned at the outset (lower reaction temperature of 235°–250° C. with ethanol, 165°–180° C. with isopropyl alcohol, lower mol ratios of water to olefin (0.3–0.4 with ethanol, 0.25–0.35 with isopropyl alcohol) as well as lower phosphoric acid content of the newly added contact (with ethanol 20–35% of the suction volume at 100% $H_3PO_4$, with isopropyl alcohol 15–25% of the suction volume at 100% $H_3PO_4$), the discharged phosphoric acid amounts are much smaller than hitherto assumed. It was thus determined that in the condensate of the reaction product on part by weight of $H_3PO_4$ is found to 800 to 1,500 parts by weight of alcohol in the case of ethanol, with isopropyl alcohol the discharged amount of phosphoric acid is still smaller, there 8,000 to 15,000 parts by weight of alcohol come to a weight part of $H_3PO_4$. This small discharge of phosphoric acid compared to the known values can be partially explained by the changed reaction conditions, for the other part, however, by the fact that one works without spraying liquid phosphoric acid onto the contact mass. When spraying liquid phosphoric said onto the contact mass, same is not distributed over the entire surface and, where it reaches the catalyst, it fills the entire pore volume with acid so that a portion of the surface of the catalyst is stripped off by the gas stream and is again removed from the reactor. A depletion of acid takes place, nevertheless, in places which are not reached.

According to the invention, the acid removal observed during the reaction does not change, however, over an extended period of time (1 to 2 weeks) without further addition of phosphoric acid to the contact mass, if the same amount of phosphoric acid as removed is added to the entering reaction gas before entry into the reactor. It is evident from the enclosed drawing, FIG. 1, how the addition of the phosphoric acid takes place in the examples. Above a gas distribution nozzle (1) the phosphoric acid is added liquidly over duct (4) into the gas stream already heated here to reaction temperature, which reaches the chamber over a perforated sheet (5). This can, for instance, take place over a simple drip pan (2) and/or over a nozzle (3) which sprays the acid finely and thus effects the distribution required during the evaporation in the hot gas stream. The joint passing of the phosphoric acid with the gas through the gas distribution nozzle causes intensive intermixing and evaporation of the phosphoric acid up to the impinging of the gas onto the contact layer. It was also discovered that the activity of the catalyst for obtaining an olefin reaction of at least 4% can be maintained in this manner with ethanol for one to two years, with isopropyl alcohol for over four years (longer experience is not available for isopropyl alcohol).

The invention is to be explained by way of the following examples:

EXAMPLE 1

1050 kilos of ethylene are reacted to 1,680 kg ethanol per hour in an installation for the production of ethanol by hydration of ethylene, consisting of a reactor filled with 18 cubic meters of silicic acid-containing support having an $H_3PO_4$ content of 38 weight %, to which 25,740 kilos of ethylene are added per hour, as well as 5,420 kilo water, so that there is a water-olefin mol ratio of 1 to 0.3, i.e., with a yield of 97%, the reaction of the inserted ethylene amounts of 4.2%. Moreover, 1.26 kilo $H_3PO_4$ are found per hour in the condensate of the reaction mixture, i.e., 1,330 parts by weight of ethanol to one weight part of $H_3PO_4$. As shown in FIG. 1, the same amount of phosphoric acid, i.e., 1.26 kilo phosphoric acid, is sprayed by way of a diluted solution per hour by way of nozzle (3). No increase in the discharged phosphoric acid amount appeared at the start of the phosphoric acid spraying. The ethylene reaction only decreased to below 4% after an operating time of 18 months, the equipment was removed and the contact was replaced by that newly saturated with phosphoric acid.

EXAMPLE 2

In an installation for the production of isopropyl alcohol by hydration of propylene consisting of a reactor filled with 20.5 cubic meter of silicic acid-containing support with an $H_3PO_4$ content of 25% by weight, to which 65,000 kilos propylene are added per hour, as well as 7,500 kilo water, so that there is a water-olefin mol ratio of 1:0.3, 2,644 kilo propylene react hourly to 3,650 kilo isopropyl alcohol, i.e., with a yield of 97%, the reaction of the inserted propylene amounts to 4.1%. In addition, 0.20 kilo $H_3PO_4$ are found per hour in the condensate of the reaction composition, i.e., 12,600 weight parts of isopropyl alcohol to one part by weight of $H_3PO_4$. As shown in FIG. 1, the same amount of phosphoric acid, i.e. 0.20 kilo phosphoric acid, is sprayed per hour by way of a diluted solution. No increase in the amount of discharged phosphoric acid appeared at the start of the phosphoric acid spraying. After a four-year operation of the installation, the average propylene reaction only decreased from originally 4.2% to 4.1%.

What is claimed is:

1. Process for the production of alcohols having two to three carbon atoms by means of catalytic hydration olefins by reaction on a catalyst comprising a support having phosphoric acid thereon, characterized in that phosphoric acid is added to the gas mixture before entry into the reactor, vaporized and in an amount corresponding to the discharged amount of phosphoric acid determined during the reaction, said process being carried out without further addition of phosphoric acid.

2. Process for the production of ethanol by catalytic hydration of ethylene according to claim 1, characterized in that one part by weight phosphoric acid is added to the gas mixture per 800 to 1,500 parts by weight of produced ethanol.

3. Process for the production of isopropyl alcohol according to claim 1, characterized in that one part weight phosphoric acid is added to the gas mixture per 8,000 to 15,000 parts by weight of produced isopropyl alcohol.

* * * * *